United States Patent [19]

Blanch

[11] Patent Number: 4,876,110
[45] Date of Patent: Oct. 24, 1989

[54] ELECTROSURGICAL KNIFE

[75] Inventor: G. Marsden Blanch, Sandy, Utah

[73] Assignee: American Medical Products, Inc., Murray, Utah

[21] Appl. No.: 83,245

[22] Filed: Aug. 10, 1987

Related U.S. Application Data

[62] Division of Ser. No. 17,876, Feb. 24, 1987.

[51] Int. Cl.$^4$ .......................... A01N 1/02; B05D 1/36; B05D 7/00; B21K 11/00
[52] U.S. Cl. ......................................... 427/2; 427/379; 427/409; 427/435; 76/104 R
[58] Field of Search ................ 76/104; 29/878; 427/2, 427/327, 379, 409, 435

[56] References Cited

U.S. PATENT DOCUMENTS

| | | | |
|---|---|---|---|
| 3,799,168 | 3/1974 | Peters | 128/303.17 |
| 4,161,950 | 7/1979 | Doss et al. | 128/303.14 |
| 4,314,559 | 2/1982 | Allen | 128/303.14 |
| 4,333,467 | 6/1982 | Domicone | 128/303.14 |
| 4,418,057 | 11/1984 | Beard | 128/303.14 |
| 4,534,347 | 8/1985 | Taylor | 128/303.17 |
| 4,545,375 | 10/1985 | Cline | 128/303.14 |
| 4,589,411 | 5/1986 | Friedman | 128/303.14 |
| 4,622,966 | 11/1986 | Beard | 30/140 |
| 4,657,016 | 4/1987 | Garito et al. | 128/303.13 |

*Primary Examiner*—Roscoe V. Parker
*Attorney, Agent, or Firm*—Sigalos, Levine & Montgomery

[57] ABSTRACT

An electrosurgical knife includes a stainless steel blade whose surface is abraded or etched, a first coat of primer material applied over the blade, where the surface of the primer material is also abraded or etched, and a second coat of non-stick fluorinated hydrocarbon material applied over the coat of primer material to cover the primer material, for a total thickness of about three mils. The stainless steel blade is completely covered by the coatings but the thickness of the coatings is not so great as to prevent conduction of radio-frequency electrical energy from the blade through the coatings to tissue being cut.

6 Claims, 1 Drawing Sheet

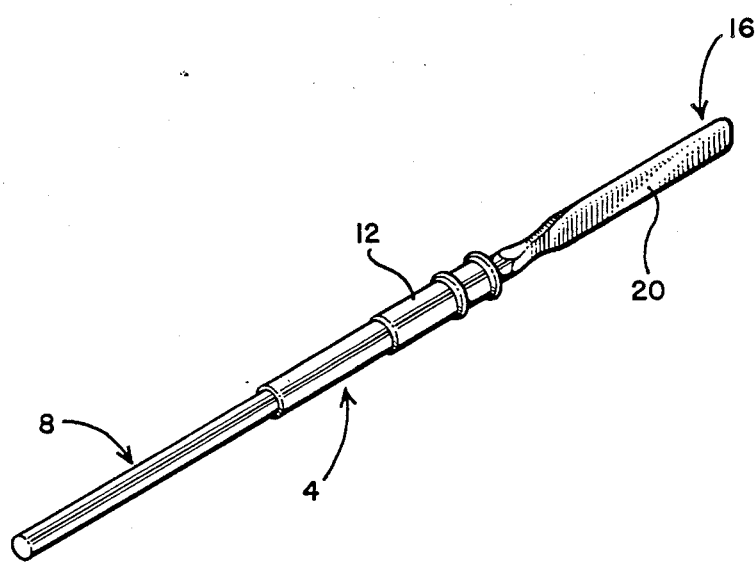

ELECTROSURGICAL KNIFE

This is a division, of application Ser. No. 07/017,876 filed Feb. 24, 1987.

BACKGROUND OF THE INVENTION

The invention relates to a new and improved electrosurgical knife coated with a non-stick material which is especially adapted to inhibit build-up of charred tissue, and a method of making same.

Electrosurgical knifes or blades currently utilized by surgeons essentially comprise a surgical steel cutting tool, such as a scalpel, and a source of radio-frequency electrical energy for application to the cutting tool. When used in surgery, the surgeon controls the application of radio-frequency electrical energy to the blade to generate heat and cause hemostasis as tissue is cut. In this manner, surgery can be carried out and bleeding minimized.

Although electrosurgical knives have proven effective for controlling bleeding during surgery, one problem which has resulted is that of tissue sticking to the blade to thereby reduce cutting efficiency and ultimately require replacement of the blade. One approach to overcoming this problem has been to coat the blade with some type of non-stick material to which cauterized tissue is less likely to adhere. Of course, such coating material must be suitable for passing electrical current or at least the coating of the material must be arranged to allow passage of current from the blade to the tissue. A sampling of prior art patents which disclose non-stick coatings for electrosurgical knifes include U.S. Pat. Nos. 4,314,559, 4,333,467, 4,161,950 and 4,481,057.

Although coating electrosurgical knife blades with non-stick material has served to improve the efficiency of surgical procedures, coated blades prepared using prior art methods still suffer from sticking problems. This is because in order to ensure electrical conductivity, small, interspersed conductive locations are provided in the coatings, i.e., small openings are allowed to form in the coating thereby exposing the metallic knife blade. In use of the knife, these conductive locations or openings typically become coated with charred tissue soon rendering the knifes nonconductive and thus unusable.

An additional problem with some of the prior art non-stick coating arrangements is the cost of applying the layers of nonstick material to the blades since typically a two layer conductive and nonconductive surface is provided for each blade, which significantly increases the cost of the blades.

SUMMARY OF THE INVENTION

It is an object of the invention to provide an electrosurgical knife having a new and improved non-stick coating.

It is an additional object of the invention to provide such a knife which may be fabricated in a simple and efficient manner.

It is a further object of the invention to provide such a knife which may be more readily cleaned of cauterized tissue for subsequent use.

It is an additional object of the invention to provide such a knife which inhibits build-up of charred tissue while surgery is being performed.

The above and other objects of the invention are realized in a specific illustrative embodiment of an electrosurgical knife adapted for use with a source of radio-frequency electrical energy to cut and cauterize tissue. The knife includes a stainless steel blade having at least one cutting edge, with the surface of the blade being abraded, a first coat of primer material applied at least to the cutting edge of the blade by dipping and then drying, and a second coat of fluorinated hydrocarbon material sold under the brand name of Teflon and known as product 455-119. This second coat of material is applied over the primer material by dipping so that the second coat has a thickness of about two mils, and then the coat is allowed to dry. The total thickness of the first and second coat is about three mils. Because of the thinness of the second coat, the coat remains conductive to radio-frequency electrical energy thus enabling the blade to cauterize tissue being cut.

BRIEF DESCRIPTION OF THE DRAWING

The above and other objects, features and advantages of the invention will become apparent from a consideration of the following detailed description presented in connection with the accompanying drawing which shows a perspective view of an electrosurgical knife made in accordance with the principles of the present invention.

DETAILED DESCRIPTION

Referring to the drawing, there is shown a conventional electrosurgical instrument to which is applied a radio-frequency signal for purposes of cauterizing or producing hemostasis simultaneously as tissue is cut. The knife 4 includes a proximal end 8 which is fitted into a holder to enable a surgeon to more readily hold and guide the knife. A sleeve fitting 12 is positioned around the knife shank to facilitate holding of the knife by the holder. The knife also includes a distal end 16 formed in the shape of a cutting blade. A coating 20 of non-stick material covers the surface area of the cutting blade and serves to eliminate or reduce the clinging of charred tissue to the blade. Although a specific surgical instrument construction is shown in the drawing and described as including the coating of the present invention, it should be understood that a variety of electrosurgical instruments could make use of and benefit from the coating as will be further described hereafter.

An exemplary procedure for fabricating the electrosurgical knife of the present invention will now be described. An extruded stainless steel cautery blade having at least one cutting edge is the base element onto which the coatings are applied. The blade itself is cleaned and dried before beginning the coating process. In particular, the blade is cleaned with a sand blast abrasive washed with a cleaning solution, and then either drip dried or blow dried with air. The blade, at least that portion which is to be coated, is then etched or abraded with about 140-grit emery paper or other similar abrasive device. All waste material produced during the etching step is wiped from the blade using a clean cloth or other material which will not shred or be torn by the blade.

That portion of the cautery blade which has been abraded is then dipped into a liquified primer material such as primer product 850-300 mixed with VM 7799, produced by Dupont. The dipping is accomplished by submerging the blade in the liquified material three times, with the blade being completely withdrawn from the material after each dip. The primer material on the blade is then blow dried with room temperature air for about 10 minutes.

After the primer material is dried, the blade is placed in a kiln oven for about 5 to 10 minutes at 450° F. After removal from the oven, the blade and primer material are allowed to cool to room temperature. The primer material is then again etched with 150-grit emery paper or similar abrasive device and wiped clean of waste material. A final coat of non-stick material is then applied, by hand dipping, over the primer material. Advantageously, a non-stick fluorinated hydrocarbon material identified as product 455-119, sold under the brand name Teflon by Dupont, is used as the coating material. The blade is dipped three times in liquified non-stick material again with the blade being withdrawn from the material between each dip. After dipping in the non-stick material, the blade and material are allowed to dry for about 1 hour at room temperature by simply keeping the dipped portion of the blade out of contact with any surface or object. The blade is then placed in a preheated oven for about 42 minutes at 750° F., after which it is removed and allowed to cool to room temperature.

The final step of the fabrication process involves polishing the second coating to a high sheen with a soft cotton cloth. This should take about five minutes and is done to remove dirt and debris and to prepare the blade to have even better non-stick properties.

By the process described, an electrosurgical knife may be fabricated with an exterior non-stick coating of about three mils total in thickness. With this thickness, radio-frequency electrical energy will conduct from the stainless steel blade through the coating to tissue being cut, to thereby cauterize the tissue. Yet, the non-stick coating also minimizes the sticking of charred tissue to the blade so that the knife can be used for longer periods of time without the need of cleaning, and can be used for more than a single surgery event. There are no openings in the non-stick coating, exposing the blade, so there is less tendency of charred tissue to stick to the blade. The process for fabricating the knives is simple and yet effective in producing a highly desirable surgical tool.

It is to be understood that the above-described arrangements are only illustrative of the application of the principles of the present invention. Numerous modifications and alternative arrangements may be devised by those skilled in the art without departing fronm the spirit and scope of the present invention and the appended claims are intended to cover such modifications and arrangements.

What is claimed is:

1. A method of fabricating an electrosurgical knife for use with a source of radio-frequency energy in cutting and cauterizing tissue, said method comprising
   (a) providing an elongate stainless steel blade having a cutting edge at one end thereof, with the other end being coupleable to an energy source,
   (b) abrading at least a portion of the surface of the blade,
   (c) applying a first coat of primer material by dipping, to at least the cutting edge of the blade,
   (d) baking the first coat,
   (e) abrading the surface of the first coat,
   (f) applying a second coat of non-stick material over the first coat by dipping, wherein the second coat is Teflon product 455-119, and
   (b) baking the second coat.

2. A method as in claim 1 wherein said primer coat is Dupont primer product 850-300 mixed with VM 7799, and wherein step (d) comprises baking for about five to seven minutes at about 450° F.

3. A method as in claim 2 wherein step (g) comprises baking for about 42 minutes at about 750° F.

4. A method as in claim 1 wherein stps (b) and (e) comprise abrading with about 140-grit emery paper or equivalent.

5. A method as in claim 1 wherein step (c) further comprises blow drying the first coat with room temperature air, and wherein step (f) further comprises drying the second coat after application thereof over the first coat and before baking.

6. A method as in claim 1 further including the step of polishing the second coat with cotton cloth.

* * * * *